(12) United States Patent
Saha

(10) Patent No.: US 12,734,060 B2
(45) Date of Patent: Sep. 15, 2026

(54) ORTHOPAEDIC IMMOBILISERS FOR RESTRICTIVE OPERATIVE MOVEMENTS

(71) Applicant: LivPrint Labs L.L.P, Pune (IN)

(72) Inventor: Kaushik Saibal Saha, Mumbai (IN)

(73) Assignee: LivPrint Labs L.L.P, Pune (IN)

( * ) Notice: Subject to any disclaimer, the term of this patent is extended or adjusted under 35 U.S.C. 154(b) by 0 days.

(21) Appl. No.: 18/806,213

(22) Filed: Aug. 15, 2024

(65) Prior Publication Data

US 2026/0047951 A1 Feb. 19, 2026

(51) Int. Cl.
*A61F 5/01* (2006.01)
*A61F 5/30* (2006.01)

(52) U.S. Cl.
CPC ............ *A61F 5/013* (2013.01); *A61F 5/0127* (2013.01); *A61F 5/30* (2013.01)

(58) Field of Classification Search
CPC .... A61F 5/00; A61F 5/01; A61F 5/013; A61F 5/0127; A61F 5/30; A61F 5/05; A61F 5/0102; A61F 5/0123; A61F 5/0125; A61F 13/04; A61F 2005/0132; A61F 2005/0137; A61F 2005/0139; A61F 2005/0146; A61F 2005/0155; A61F 2005/0158; A61F 2005/0165; A61F 2005/0167; A61F 2005/0169; A61F 2005/0174; A61F 2005/0175; A61F 2005/0179; A61F 2005/0181; A61F 2005/0197
See application file for complete search history.

(56) References Cited

U.S. PATENT DOCUMENTS

2009/0287127 A1* 11/2009 Hu ........................ A61F 5/0111 602/27
2010/0049110 A1* 2/2010 Blanchard ........... A61F 5/05841 602/20
2014/0039372 A1* 2/2014 Blue ..................... A61F 5/0118 602/21
2014/0316316 A1* 10/2014 Andrews ............... A61F 13/043 602/12
2018/0257276 A1* 9/2018 Hipwood ............... A43C 11/00
2019/0365554 A1* 12/2019 Davies-Sekle ....... A61H 1/0281
2020/0197209 A1* 6/2020 Bejarano ............... A61F 5/0125
2023/0263592 A1* 8/2023 Settele ................ A63B 71/085 128/861
2025/0195939 A1* 6/2025 Wang ................. A63B 21/0054

* cited by examiner

*Primary Examiner* — Alireza Nia
*Assistant Examiner* — Gina Mccarthy
(74) *Attorney, Agent, or Firm* — Preston Smirman; SMIRMAN IP LAW, PLLC

(57) ABSTRACT

Orthopaedic immobilizers 100 that help in infliction relief, healing and rehabilitation and allow restrictive operative movements. These include bicep unit 130, forearm unit 140, full arm unit 150, formed by connecting bicep unit 130 with the forearm unit 140 with the help of a rotor unit 116 and ankle unit 160. The immobilizers 100 consist of two separate independent parts-first part 102 and the second part 104 that are locked together by locking means that facilitates tightening or loosening around the anatomy of body part where it is used for. The parts 102, 104 have a plurality of slots for the locking means 106 on the edge surfaces and they consist of plurality of breathable openings 114 that allow for the observations and examination without any need to open or slit the immobilizer 100 and they have a medical grade foam padding on the internal lining.

7 Claims, 10 Drawing Sheets

ORTHOPAEDIC IMMOBILISERS FOR RESTRICTIVE OPERATIVE MOVEMENTS

FIELD OF THE INVENTION

The present invention relates to orthopaedical immobilizers and more particularly relates to orthopaedical immobilizers that are used during infliction relief, healing and rehabilitation and allow restrictive operative movements for the users.

BACKGROUND OF THE INVENTION

Today's orthopaedic industry and market has an array of products that cater to varied use-cases and needs of a patient. But in the fracture and break scenario, the products used in the existing industry are still dated; carrying with it dated features and benefits and restrictions.

The fracture and break market does currently not have a prefabricated cast or splint that can be used as an immediate appliance at the medical practitioner or physiotherapist or in any emergency situation, for the most widely occurring and most-common cases. The currently available splints and braces are not rigid enough to provide complete and absolute immobilization.

When a fracture occurs, the attending medical practitioner first conducts a manual reduction of the displaced or broken bones. This involves the medical practitioner to adjust and align the bones in the affected area of the anatomy with their bare hands, with pressure and compression techniques. The first product that is applied onto the anatomy in most cases is either a cast or a splint. A splint is used in case of a swelling. A splint is usually made with cardboard or tough paper strips. Reason being, if the swelling was not present, then it's nothing different than a cast, as it has to be rigid. But because the splint must stay on the anatomy till the swelling subsides, whilst keeping the anatomy immobilized, splints in the current usage are a temporary-usage product for about 6 days to 10 days. But this just adds another product in the treatment life cycle unnecessarily. Then the patient has to wait for the swelling to subside in a few days. Then the patient must come back to the medical practitioner and apply a rigid cast. The most used rigid cast is either a fiberglass band, blue cast or a plaster of Paris cast. Plaster of Paris is still the most used product. A cast cannot be used or applied on a swollen fractured/broken anatomy whilst the swelling is present as the cast will gradually begin to offer a loose fit on the anatomy as and when the swelling subsides, due to the space and gaps that will begin to appear between the anatomy and cast.

A cast in most cases is cut open for examination by the medical practitioner, or in a lot of cases, reapplied and changed (due to swelling reduction or the cast getting wet or damaged). In summary, multiple casts are to be used till the final healing stage and this incurs multiple application fees/product charge to the patients.

Usually, after a fracture has healed and the bones are aligned, the medical practitioners/physiotherapist begins the process of rehabilitation of the affected anatomy. This involves an array of procedures; exercise, articulated and restricted movement of anatomy, traction & strength regaining regimes etc. During this course and time, the medical practitioner tends to shift to another product. Either a functional brace or an ROM enabled brace. In other words, these are products that provide stability, guided movement and supported articulation etc. These products usually come fit with a rotary mechanism of sorts, the helps the anatomy rotate/revolve, and more importantly, define a pre locked angle of motion that helps the affected part of the anatomy regain normal flexion and movement.

OBJECTS OF THE INVENTION

A primary object of the present invention is to provide orthopaedic immobilizers.

Another object of the present invention is to provide orthopaedic immobilizers that are used during infliction, healing and rehabilitation and allow restrictive operative movements for the users.

Another object of the present invention is to provide orthopaedic immobilizers that are rigid and at the same time can capacitate for size and swelling.

Yet another object of the present invention is to provide orthopaedic immobilizers that need not be cut open for examination by medical practitioners.

Another object of the present invention is to provide orthopaedic immobilizers that are water resistant, resistant to external trauma or any impact from external object, non-reactive to earthly elements and hypoallergenic.

Another object of the present invention is to provide orthopaedic immobilizers that transition from a splint to a cast seamlessly, without any product alterations.

Yet another object of the present invention is to provide orthopaedic immobilizers that are used as a splint in case of a fracture/break to manage swelling and bloating of the anatomy and the same immobilizers transition into a cast after the swelling subsides, thus eliminating the need to apply external cast material.

SUMMARY OF THE INVENTION

Before the present invention is described, it is to be understood that present invention is not limited to particular methodologies and materials described, as these may vary as per the person skilled in the art. It is also to be understood that the terminology used in the description is for the purpose of describing the particular embodiments only and is not intended to limit the scope of the present invention.

In a preferred embodiment of the present invention, the orthopaedical immobilizers of the present invention for infliction relief, healing and rehabilitation and that allow restrictive operative movements for the users. The orthopaedic immobilizers include bicep unit, forearm unit, full arm unit and ankle unit. The bicep unit connects with the forearm unit with the help of a rotor unit to form the full arm unit. The orthopaedic immobilizers consist of two separate independent parts-first part and the second part that are locked together by locking means that facilitates tightening or loosening around the anatomy of body part where it is used for. The parts have a plurality of slots for the locking means on the edge surfaces. The parts consist of plurality of breathable openings of different shapes and sizes depending on the type of the orthopaedic immobilizers and these openings allow for the observations and examination without any need to open or slit the immobilizer and the parts have a medical grade foam padding on the internal lining.

In the preferred embodiment of the present invention, the rotor unit comprises of at least two rotor blades aligned together and fixed at one end by the rotor hub by screws on the rotor hub and the rotor blades further consist of plurality of holes for screw tightening that allow for the rotor unit to be locked at multiple angles and allows a certain range of motion or movement of the immobilizers. The rotor unit is adjusted to select a desired angle and range of motion such as during the casting stage, the rotor unit stays locked and all the screws are tightened to avoid any movement and post healing, during the rehabilitation stage, the same rotor unit is articulated for free movement and defined angle range.

In the preferred embodiment of the present invention, in the full arm unit, the first part and the second part of the bicep unit and the forearm are connected with the respective corresponding parts by two rotor units and on each part, the rotor blade of the rotor unit slide through the slots for rotor blade and are fixed with the bicep unit and the forearm unit by screws tightened in the four-screw block.

In the preferred embodiment of the present invention, the features such as foam padding inside the immobilizers, traction resistant silicone fasteners with size allocation with all the immobilizers and multiple locking points that allow the medical practitioner to tighten or loosen the immobilizer on the anatomy as desired, allow the immobilizer to begin its life cycle as a splint. This gives the medical practitioner and the user both, time to subside the swelling and then come back for the appliance of a cast, which is the same immobilizer. Features of the immobilizers of the present invention such as rigid external architecture (medical grade nylon+PE) and cable-locks/tie-locks for absolute locking of product allow these immobilizers to exhibit the characteristics of a traditional fiber glass or Plaster of Paris cast. The locks prohibit any movement, whilst the rigid architecture forms a cast and shell around the affected anatomy.

BRIEF DESCRIPTION OF THE DRAWINGS

A complete understanding of the present invention may be made by reference to the following detailed description which is to be taken in conjugation with the accompanying drawing. The accompanying drawing, which is incorporated into and constitutes a part of the specification, illustrates one or more embodiments of the present invention and, together with the detailed description, it serves to explain the principles and implementations of the invention.

DETAILED DESCRIPTION OF THE INVENTION

Figure 1A:
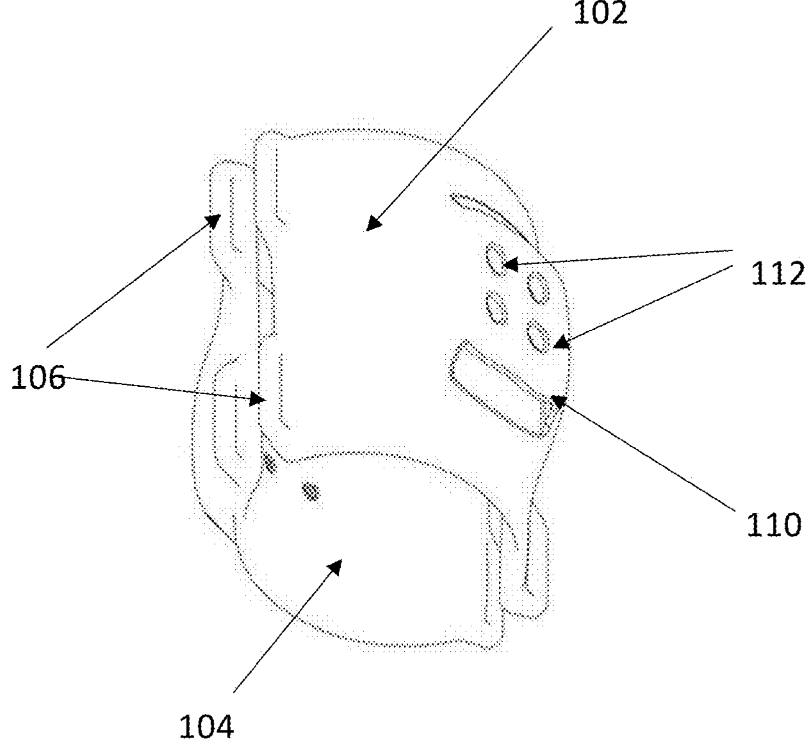
FIGS. 1*a*, 1*b*, 1*c* and 1*d* are perspective views of the different types of immobilizers according to an embodiment of the invention.
Figure 1B:
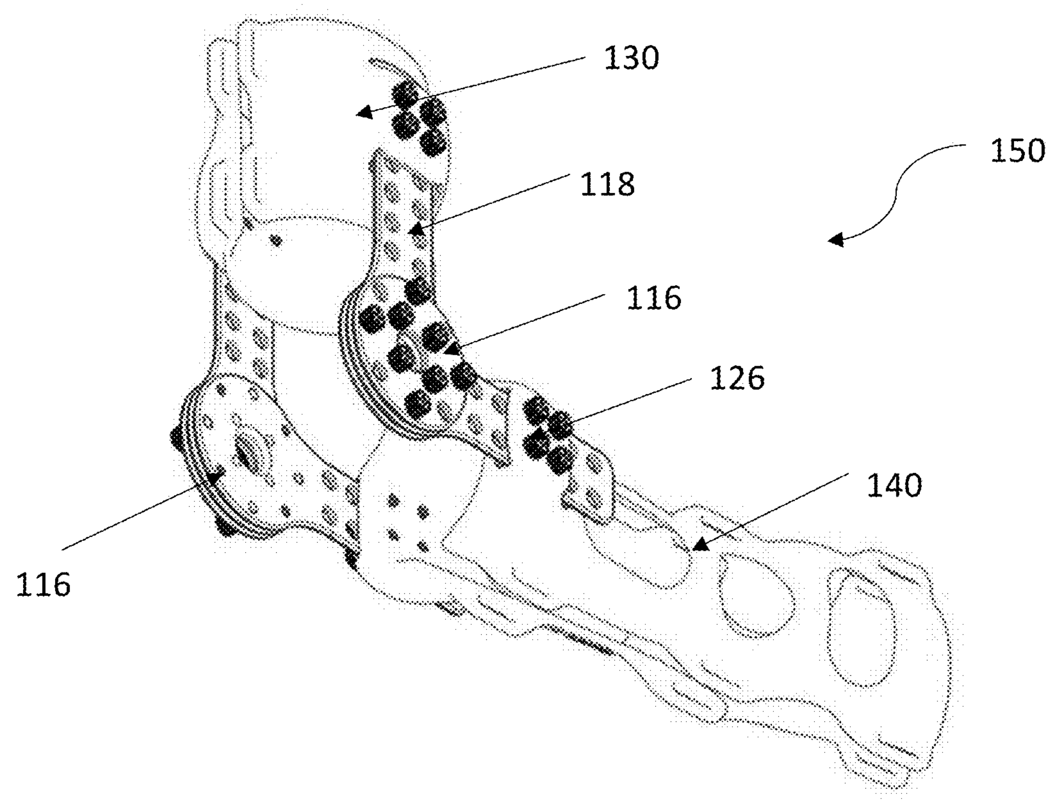
Figure 1C:
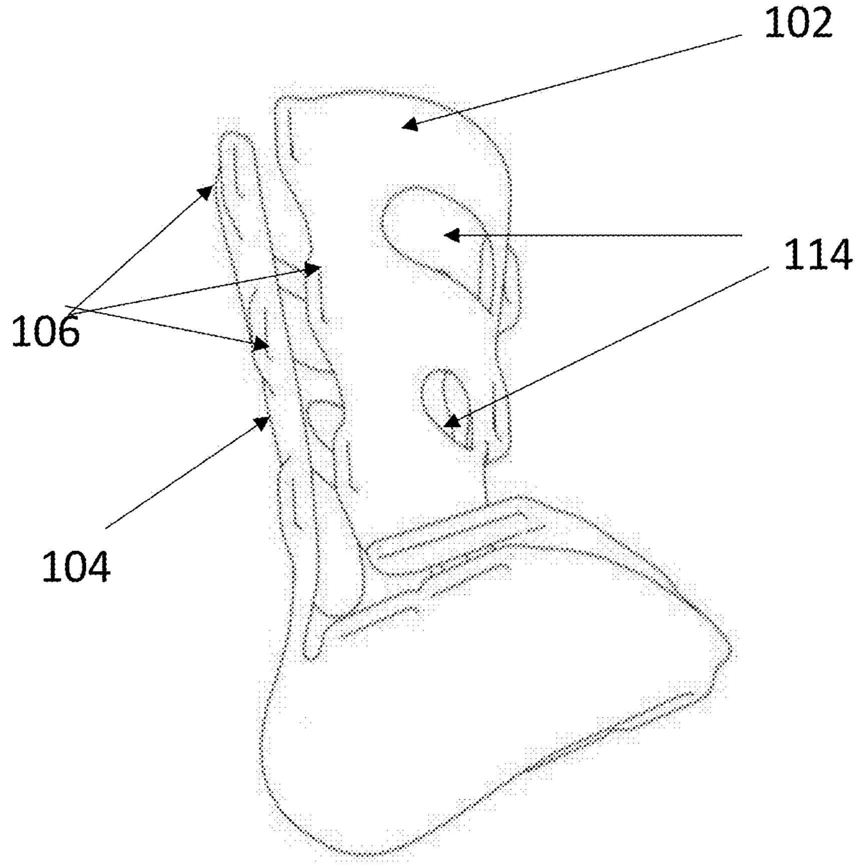
Figure 1D:
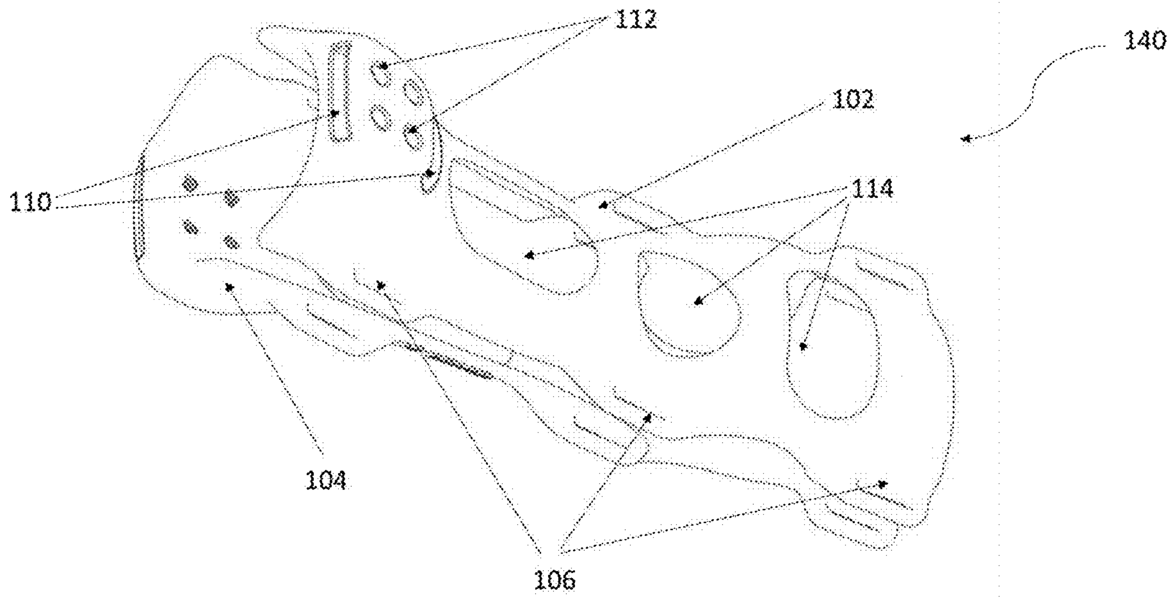

Before the present invention is described, it is to be understood that this invention is not limited to particular methodologies described, as these may vary as per the person skilled in the art. It is also to be understood that the terminology used in the description is for the purpose of describing the particular embodiments only and is not intended to limit the scope of the present invention. Throughout this specification, the word "comprises", or variations such as "comprises" or "comprising", will be understood to imply the inclusion of a stated element, integer or step, or group of elements, integers or steps, but not the exclusion of any other element, integer or step, or group of elements, integers or steps. The use of the expression "at least" or "at least one" suggests the use of one or more elements or ingredients or quantities, as the use may be in the embodiment of the invention to achieve one or more of the desired objects or results.

The present invention describes orthopaedical immobilizers that are used during infliction, healing and rehabilitation and allow restrictive operative movements for the users. In the case of a fracture/break, depending on the anatomy affected, the orthopaedical immobilizers are used by the users/patients, on recommendation and advise of a medical practitioner, as a splint to manage swelling and bloating of anatomy. After the swelling subsides, the same orthopaedic immobilizers, due to their rigid and non-flexible design transition into a cast. No additional external material is required to be used with the immobilizers to be used a cast. The immobilizers function as a split and accommodate for swelling and bloating of anatomy. The same immobilizers also function as a cast to keep the affected anatomy absolutely immobilized.

In the given embodiment of the present invention, the orthopaedic immobilizers are for various parts of human body that are prone to fracture/break or any type of impact that requires external assistance to repair and heal such as ankles, wrists, arms, legs, etc. The orthopaedic immobilizers described in the present invention include but are not limited to bicep unit, forearm unit, ankle unit, full arm unit. The immobilizers of the present invention are ambidextrous and can be used on both left and right body parts. The immobilizers are also manufactured in varied sizes such as small, medium and large to accommodate all shapes and sizes of the injured anatomies or body parts.

In the given embodiment of the present invention, as described in FIGS. 1*a*, 1*b*, 1*c* and 1*d*, the orthopaedic immobilizers 100 include but are not limited to the bicep unit 130, forearm unit 140, full arm unit 150 and ankle unit 160. All the types of orthopaedic immobilizers 100 have common constructional features and only the size and shape of the immobilizer differs based on the part of the body where it is used for. The bicep unit 130 is for the biceps area of the arm of the human body. The forearm unit 140 is used for the radial and the ulna region of the forearm of the body. The bicep unit 130 and forearm unit 140 together are used in a combination along with a rotor unit 116 to form a full arm unit 150. The full arm unit 150 is mainly used for elbow region and the full arm region. The ankle unit 160 is for the ankle region of the leg.

Figures 2A, 2B:
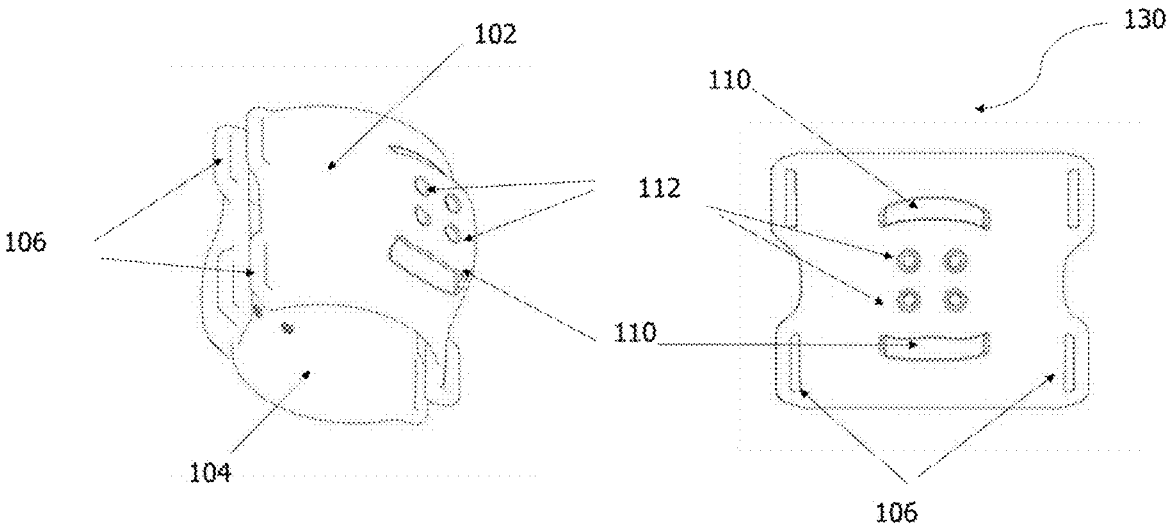
FIG. 2*a* is a perspective view of the immobilizer-bicep unit and FIG. 2*b* is the front view of the immobilizer-bicep unit according to an embodiment of the invention.
Figure 3:
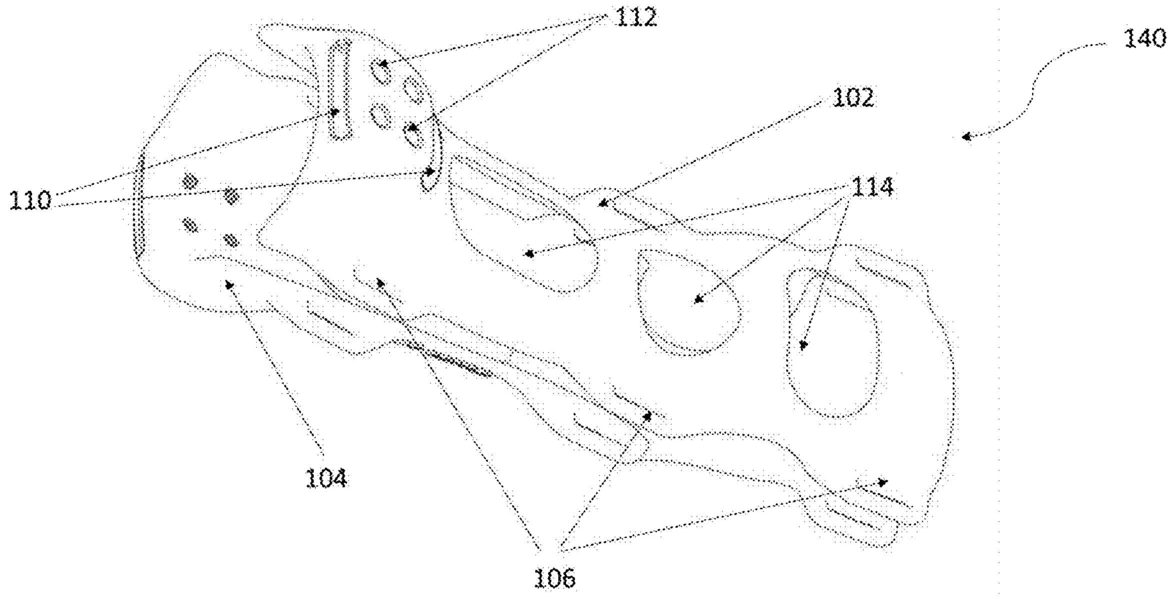
FIG. 3 is a perspective view of the immobilizer-forearm unit according to an embodiment of the invention.
Figure 4:
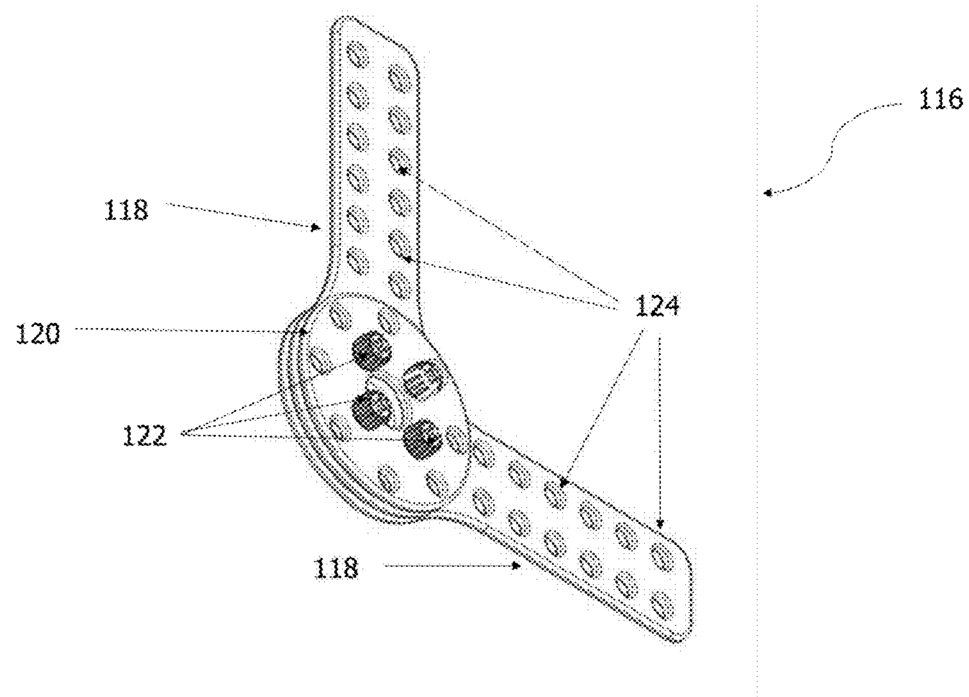
FIG. 4 is a perspective view of the rotor unit used in the immobilizer according to an embodiment of the invention.
Figure 5A:
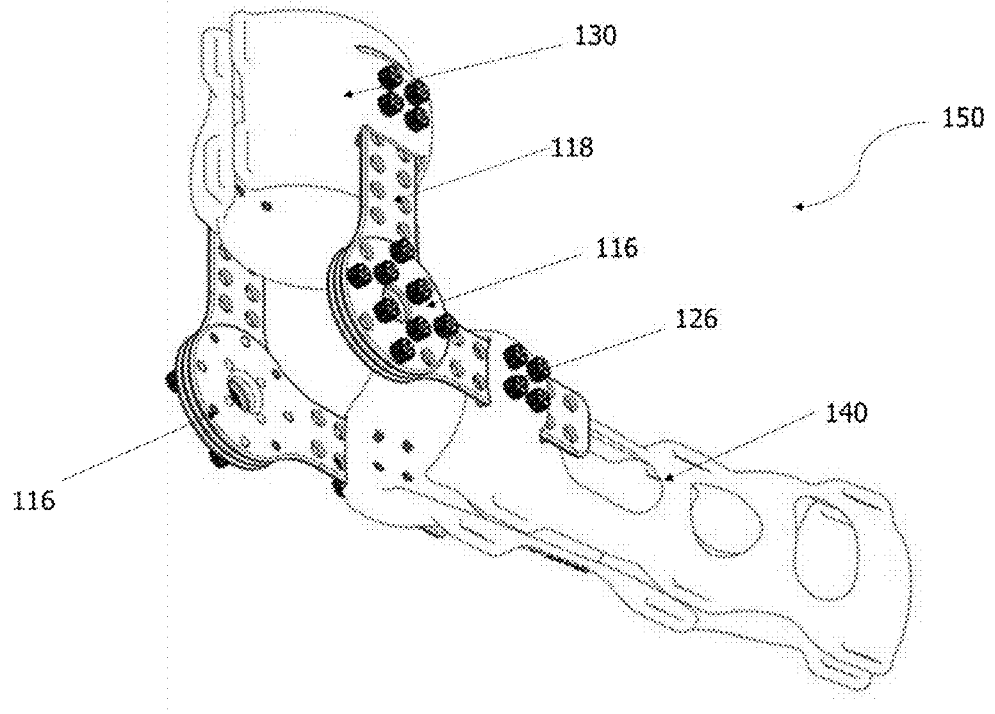
FIG. 5*a* is a perspective view of the immobilizer-full arm unit and FIG. 5*b* is a front view of the immobilizer-full arm unit according to an embodiment of the invention.
Figure 5B:
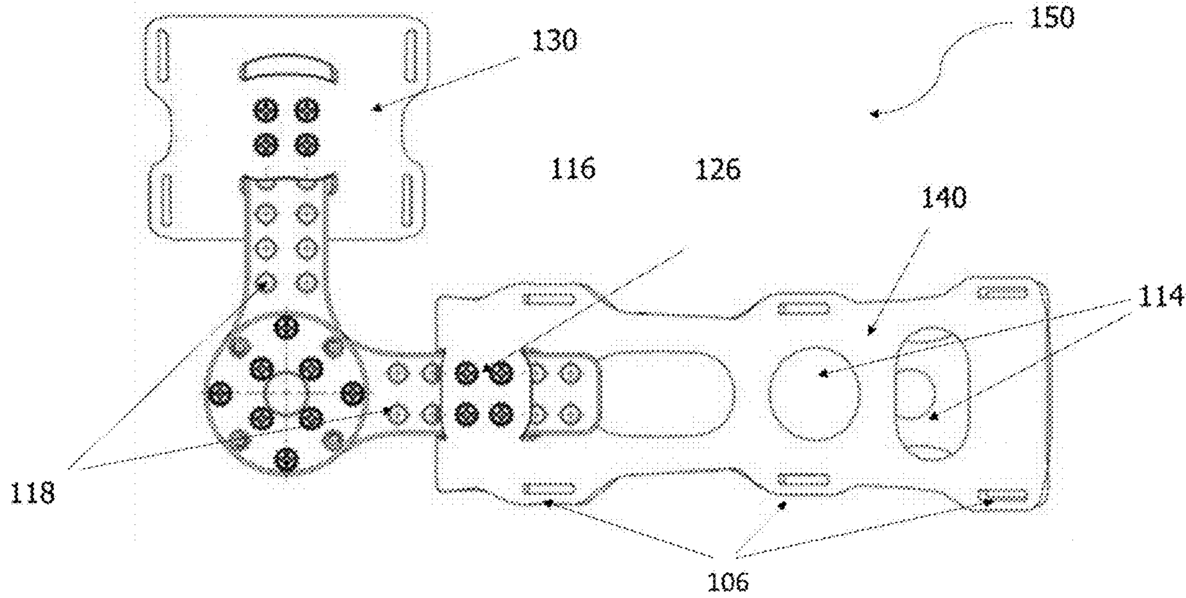
Figures 6A, 6B:
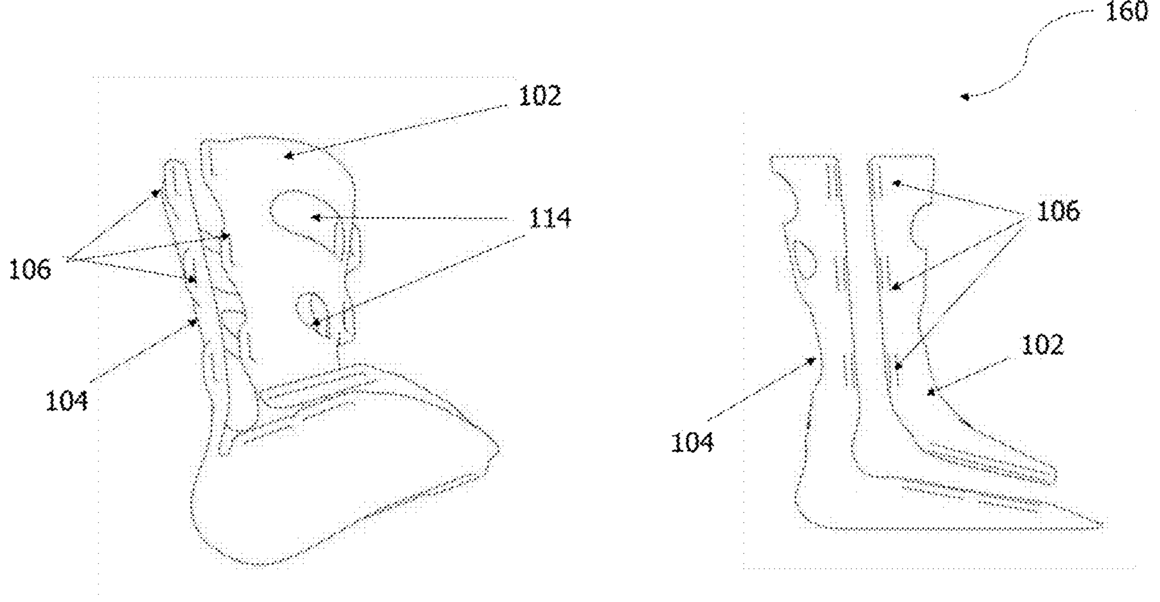
FIG. 6*a* is a perspective view of the immobilizer-ankle unit and FIG. 6*b* is a front view of the immobilizer-ankle unit according to an embodiment of the invention.

In the given embodiment of the present invention, FIGS. 2*a* and 2*b* illustrate the bicep unit 130, FIG. 3 is the perspective view of the forearm unit 140, FIG. 4 is the perspective view of the rotor unit 116 used in the different types of immobilizers; FIGS. 5*a* and 5*b* illustrate the full arm unit 150 and FIGS. 6*a* and 6*b* illustrate the ankle unit 160.

In the given embodiment of the present invention, all the types of orthopaedic immobilizers 100 consist of two separate parts. These are the first part 102 and the second part 104. The two-part design of the immobilizers facilitates tightening or loosening around the anatomy of body part where it is used for. Both the parts 102, 104 are independent and are locked together by locking means (not shown in the Figures). The locking means include but are not limited to straps, industrial grade Velcro and buckles, traction resistant silicone fasteners, and tie-locks. The parts 102, 104 also have a plurality of slots for the locking means 106 on the edges of the parts 102, 104. The first part 102 and the second part 104 consist of plurality of breathable openings 114. These openings are of various shapes and sizes depending on the type of the orthopaedic immobilizers. These openings 114 on the immobilizers allow for the medical practitioner's observations and examination without any need to open or slit the immobilizer. These openings 114 also allow for electro-pulse treatment. The first part 102 and the second part 104 of the immobilizers are made of hypoallergenic materials including but not limiting to medical grade nylon, polypropylene glass filled, polyethylene and Delrin. These materials are non-reactive to skin and even suitable to patients with skin rashes/allergies. Further, foam padding is provided on the inner surface of the first and second part 102, 104 in all the types of immobilizers. Hypoallergenic EVA (Ethylene vinyl acetate) medical grade foam is used for snug fit.

In the given embodiment of the present invention, FIG. 2*a* is the perspective view of the immobilizer-bicep unit 130 and FIG. 2*b* is the front view of the immobilizer-bicep unit 130. The bicep unit 130 is used for the biceps area of the arm of the human body. The bicep unit 130 consists of the concavely curved first part 102 and the convexly curved second part 104 to resemble the shape of a typical bicep region where it is to be used. The first part 102 and the second part 104 further comprises of mainly four slots for locking means 106 on the four corners and in the center, there is a four-screw block 112 with slots for rotor blade 110 present on each end of the four-screw block 112.

In the given embodiment of the present invention, FIG. 3 is the perspective view of the immobilizer-forearm unit 140. The forearm unit 140 also comprises of the first part 102 and the second part 104 corresponding to the radial and ulna region of the forearm of the human body respectively. This immobilizer is mainly used for Radial forearm fracture, Ulna forearm fracture, Soft-tissue damage, to immobilize joints of hand and wrist, for sprains/aches, during post-operative conditions or for temporary immobilization. The first 102 and second part 104 comprises of a plurality of breathable openings 114 on its surface and at least three slots for locking means 106 on its edges. The four-screw block 112 are holes for screw tightening and is present at the elbow side of the forearm unit 140. Further, slots for rotor blade 110 are also present on the two ends of the four-screw block 112 to align and fix the rotor unit 116.

In the given embodiment of the present invention, FIG. 4 is the perspective view of the rotor unit 116 used in the immobilizers 100. The rotor unit 116 mainly comprises of at least two rotor blades 118 aligned together and fixed at one end by the rotor hub 120. The rotor blades 118 are fixed at an angle by screws on the rotor hub 122. The rotor blades further consist of plurality of holes for screw tightening 124. The rotor unit 116 when used with the immobilizers 100 allows for free-flow movement. The plurality of holes for screw tightening 124 allows for the rotor unit to be locked at multiple angles. The rotor unit can be preassembled for faster usage and application and also allows for adjustable height and forward movement. The rotor unit 116 is made of nylon and the screws for tightening are M4 screws with custom knob heads. The rotor unit 116 is lockable at multiple angles and can also be used to allow a certain range of motion or movement. The robust screw locking keeps the rotor unit 116 rigid and always stable when used with the immobilizers. The rotor unit used with the immobilizers can be locked at multiple angles. The rotor unit can also be kept unlocked for free-flow and non-restricted movement. The rotor unit can be adjusted to select a desired angle and range of motion by the medical practitioner. For example, during the casting stage, the rotor unit stays locked, and all the screws are tightened to avoid any movement. Post healing, when into rehabilitation stage, the same rotor unit can be articulated for free movement and defined angle range.

In the given embodiment of the present invention, FIG. 5*a* is the perspective view of the full arm unit 150 and FIG. 5*b* is the front view of the full arm unit 150. The forearm unit 150 fits in the entire region of the arm of the human body. It is mainly used during radius and ulna (proximal/mid/distal) fracture. The use of full arm unit 150 prevents pronation and supination of forearm and helps to immobilize or restrict the movement of elbow during injury. It also helps during rehabilitation and recovery by facilitating guided/articulated movement of elbow by preventing flex and extension of elbow. It is also useful during any soft tissue damage. The bicep unit 130 connects with the forearm unit 140 with the help of rotor unit 116 to form the full arm unit 150. The first part 102 and the second part 104 of the bicep unit 130 and the forearm 140 are connected with the respective corresponding parts by two rotor units 116. On each part 102, 104, the rotor blades 118 of the rotor unit 116 slide through the slots for rotor blade 110 and are fixed with the bicep unit 130 and the forearm unit 140 by screws 126 tightened in the four-screw block 112. The screws on the rotor hub 122 are tightened or loosened depending on the angle of the immobilizer required for the particular case. Because of plurality of holes 124 present on the rotor blades 118 of the rotor unit 116 the rotor unit 116 can be shifted front/back for size adjustment. The full arm unit 150 protects the elbow region of the human body and immobilizes the arm to allow for no or restrictive movement depending on the stage of injury or recovery of the full arm or elbow.

In the given embodiment of the present invention, FIG. 6 is the perspective view of the ankle unit 160. The ankle unit 160 fits in the lower leg and the ankle region of the human body and is designed to accommodate the feet as well for ease of use and comfort. The ankle unit 160 helps to prevent dorsiflexion and plantar flexion, inversion and eversion of ankle joint. It assists to stabilize and immobilize the ankle joint and also provides temporary splinting. It can be used during post-operation conditions and also for rehabilitation of soft-tissue or muscle. The ankle unit 160 has a curved heel and a flat sole base. The first 102 and second part 104 of the ankle unit 160 comprises of a plurality of breathable openings 114 on its surface and at least four slots for locking means 106 on its edges. The two separate parts 102 and 104 allow for ease of application and are fixed together by the locking means according to the size requirement and the condition of the anatomy.

In the given embodiment of the present invention, the several types of immobilizers 100 are prepared by using molds. The molds for different shapes of immobilizers are made with pre hardened P20 metal with a mix of alloys and metal ribs at juncture places for extra support and rigidity. The injection molds are transferable and portable for use.

In the given embodiment of the present invention, the features such as foam padding inside the immobilizers, traction resistant silicone fasteners with size allocation with all the immobilizers and multiple locking points that allow the medical practitioner to tighten or loosen the immobilizer on the anatomy as desired, allow the immobilizer to begin its life cycle as a splint. This gives the medical practitioner and the user both, time to subside the swelling and then come back for the appliance of a cast, which is the same immobilizer. Features of the immobilizers of the present invention such as rigid external architecture (medical grade nylon+PE) and cable-locks/tie-locks for absolute locking of product allow these immobilizers to exhibit the characteristics of a traditional fiberglass or Plaster of Paris cast. The locks prohibit any movement, whilst the rigid architecture forms a cast and shell around the affected anatomy.

Advantages

- The orthopaedical immobilizers of the present invention function as a splint, cast and rehabilitation product.
- These different uses of the same immobilizer eliminate the costs of multiple product applications at various stages of healing and eliminates multiple cast applications at various stages of healing.
- The orthopaedical immobilizers of the present invention provide ease of examination of the anatomy for the medical practitioners due to open-design architecture and easy unlocking straps.
- The orthopaedical immobilizers of the present invention are waterproof, thus making them favorable for users to wear during showers and monsoon etc. (The conventional cast material is rendered damaged and useless even if it gets wet slightly, as it loses its shape and rigidity).
- The orthopaedical immobilizers of the present invention are made from hypoallergenic material and therefore it is non-reactive to skin, open wounds, and allergies.
- The orthopaedical immobilizers of the present invention have multiple locking systems that capacitate for swelling.
- In-built rotary systems in the orthopaedical immobilizers allow for multiple use-cases.
- The orthopaedical immobilizers of the present invention can be used in trauma, ER, Post or pre surgery as an emergency-response-product.
- The orthopaedical immobilizers of the present invention is portable and doesn't require multiple accessories (conventional cast material needs water, a container, a dryer, and a working table for application), apart from a host of other small accessories like scissors, tapes, gloves, spare cloth, etc.

The embodiments herein above and the various features and advantageous details thereof are explained with reference to the non-limiting embodiments in the following description. Descriptions of well-known components and processing techniques are omitted to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully revealed the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for description and not of limitation. Therefore, while the embodiments herein have been described in terms of preferred embodiments, those skilled in the art will recognize that the embodiments herein can be practiced with modification within the scope of the embodiments as described herein.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

LIST OF REFERENCE NUMERALS

| Sr. No. | Description of the part |
|---|---|
| 100 | orthopaedic immobilizer |
| 102 | first part of the orthopaedic immobilizer |
| 104 | second part of the orthopaedic immobilizer |
| 106 | slots for locking means |
| 110 | slots for rotor blades |
| 112 | four screw block on first part |
| 114 | breathable openings |
| 116 | rotor unit |
| 118 | rotor blades |
| 120 | rotor hub |
| 122 | screws on rotor hub |
| 124 | holes on rotor blade for screw tightening |
| 126 | screws tightened in the four-screw block |
| 130 | bicep unit |
| 140 | forearm unit |
| 150 | full arm unit |
| 160 | ankle unit |

What is claimed is:

1. An orthopaedic immobilizer system for infliction relief, healing and rehabilitation and that allow restrictive operative movements for the users, comprising:

a plurality of different orthopaedic immobilizers including a bicep unit, a forearm unit, a full arm unit and an ankle unit;

wherein the bicep unit is selectively operable to connect with the forearm unit to form the full arm unit;

wherein the orthopaedic immobilizers include a first part and a second part that are selectively operable to be locked together by locking means that is configured to facilitate tightening or loosening around an anatomy of a body part where it is used for;

wherein the first and second parts include a plurality of breathable openings of different shapes and sizes depending on a type of the orthopaedic immobilizers, wherein the openings allow for observation and examination without any need to open or form an opening on the orthopaedic immobilizers;

wherein the first and second parts have foam padding on an internal lining thereof;

wherein in the full arm unit, the first and second parts of the bicep unit and the forearm unit are connected with their respective corresponding parts by spaced and opposed first and second rotor units;

wherein a first pair of rotor blades of the first rotor unit are selectively operable to slide through a slot formed on the first and second parts of the bicep unit;

wherein, a second pair of rotor blades of the second rotor unit are selectively operable to slide through a slot formed on the first and second parts of the forearm unit;

wherein the first and second pair of rotor blades are selectively operable to be fixed at variable lengths thereof with the bicep unit and the forearm unit by fasteners tightened in a fastener block formed on the first and second parts of the bicep unit and the first and second parts of the forearm unit, respectively;

wherein the first and second rotor units are selectively operable to be secured in a fixed position relative to the bicep unit or the forearm unit by a plurality of fasteners tightened through a plurality of holes formed in a rotor hub formed on the first and second rotor units, wherein the first and second rotor units are selectively operable to be secured in a plurality of angles to permit a predetermined range of motion or movement of the orthopaedic immobilizers.

2. The orthopaedic immobilizer system as claimed in claim 1, wherein the bicep unit is configured for a biceps area of the arm, the forearm unit is configured for a radial and ulna region of the forearm, the full arm unit is configured for an elbow region and a full arm region and the ankle unit is configured for an ankle region of the leg.

3. The orthopaedic immobilizer system as claimed in claim 1, wherein the first and second rotor units are selectively operable to be adjusted to select a desired angle and range of motion during a casting stage, wherein the first and second rotor units are selectively operable to stay locked and all the fasteners are selectively operable to be tightened to avoid any movement during a post healing stage, and wherein during a rehabilitation stage, the first and second rotor units are selectively operable to be articulated for free movement and a defined angle range.

4. The orthopaedic immobilizer system as claimed in claim 1, wherein the ankle unit has a curved heel and a flat sole base and first and second parts, wherein the first and second ankle parts of the ankle unit comprise a plurality of breathable openings on a surface and at least four slots for locking means on its edges and the first and second parts allow for ease of application and are fixed together by the locking means according to a size requirement and a condition of the anatomy.

5. The orthopaedic immobilizer system as claimed in claim 1, wherein the locking means include straps, hook and loop fasteners and buckles, traction resistant silicone fasteners, and tie-locks.

6. The orthopaedic immobilizer system as claimed in claim 1, wherein the first and second parts of the orthopaedic immobilizers are made of hypoallergenic materials including medical grade nylon, glass filled polypropylene, polyethylene and polyoxymethylene.

7. The orthopaedic immobilizer system as claimed in claim 1, wherein the plurality of different orthopaedic immobilizers are prepared by using injection molds that are made with pre-hardened P20 metal with a mix of alloys and metal ribs at juncture places for extra support and rigidity and the injection molds are transferable and portable for use.

* * * * *